(12) United States Patent
Patel et al.

(10) Patent No.: US 8,539,944 B2
(45) Date of Patent: Sep. 24, 2013

(54) DEVICES AND METHODS FOR NEBULIZING FLUIDS FOR INHALATION

(75) Inventors: Rajan Patel, Union City, CA (US); Michael A. Klimowicz, Escondido, CA (US)

(73) Assignee: Novartis AG, Basel (CH)

( * ) Notice: Subject to any disclaimer, the term of this patent is extended or adjusted under 35 U.S.C. 154(b) by 848 days.

(21) Appl. No.: 12/099,302

(22) Filed: Apr. 8, 2008

(65) Prior Publication Data
US 2008/0184993 A1 Aug. 7, 2008

Related U.S. Application Data

(62) Division of application No. 10/338,194, filed on Jan. 7, 2003, now Pat. No. 7,360,536.

(60) Provisional application No. 60/346,789, filed on Jan. 7, 2002, provisional application No. 60/403,454, filed on Aug. 13, 2002.

(51) Int. Cl.
*A61M 11/00* (2006.01)
(52) U.S. Cl.
USPC .................................. 128/200.14; 128/200.22
(58) Field of Classification Search
USPC ............. 128/200.14, 200.17, 200.19, 200.21, 128/200.23, 203.12, 203.14, 203.15, 203.19, 128/203.23–203.25, 203.28; 604/48, 59, 604/140, 141, 254, 275; 202/309, 390; 239/338
See application file for complete search history.

(56) References Cited

U.S. PATENT DOCUMENTS

| 550,315 | A | 11/1895 | Allen |
| 809,159 | A | 1/1906 | Willis et al. |
| 1,680,616 | A | 8/1928 | Horst |
| 2,022,520 | A | 11/1935 | Philbrick |
| 2,101,304 | A | 12/1937 | Wright |
| 2,158,615 | A | 5/1939 | Wright |
| 2,187,528 | A | 1/1940 | Wing |
| 2,223,541 | A | 12/1940 | Baker |

(Continued)

FOREIGN PATENT DOCUMENTS

| CH | 477 855 | 9/1969 |
| CH | 555 681 | 11/1974 |

(Continued)

OTHER PUBLICATIONS

Aulton, M.E., "Chapter 20—Therapeutic Aerosols," Pharmaceutics, The Science of Dosage Form Design, pp. 341-358, 1988.

(Continued)

*Primary Examiner* — Kristen Matter
(74) *Attorney, Agent, or Firm* — Michael J. Mazza

(57) ABSTRACT

A method of delivering a nebulized fluid for inhalation, including providing an aerosol generator, providing a container containing a fluid to be nebulized, providing a reservoir in fluid communication with the container and with the aerosol generator, providing a moveable member positioned to act upon the container in a manner to elect fluid therefrom, providing a linkage mechanism operable through a range of operating positions that is coupled to the moveable member to selectively control a distance of movement of the moveable member, selecting the distance of movement of the moveable member, moving the moveable member to eject fluid from the container into the reservoir, and operating the aerosol generator to elect fluid from the reservoir as a nebulized fluid for inhalation.

7 Claims, 6 Drawing Sheets

(56) References Cited

U.S. PATENT DOCUMENTS

| | | |
|---|---|---|
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singier |
| 3,353,537 A | 11/1967 | Knox et al. |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,690,317 A | 9/1972 | Millman |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,838,686 A | 10/1974 | Szekely |
| 3,842,833 A | 10/1974 | Ogle |
| 3,858,739 A | 1/1975 | Turner et al. |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,030,492 A | 6/1977 | Simbruner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rosenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,443,945 A | 4/1984 | Takemura et al. |
| 4,454,877 A | 6/1984 | Miller et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,512,341 A | 4/1985 | Lester |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A | 10/1987 | Carter et al. |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,823,784 A | 4/1989 | Bordoni et al. |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,883,472 A | 11/1989 | Michel |
| 4,888,516 A | 12/1989 | Daeges et al. |
| 4,922,901 A | 5/1990 | Brooks et al. |
| 4,926,915 A | 5/1990 | Deussen et al. |
| 4,934,358 A | 6/1990 | Nilsson et al. |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |
| 4,973,493 A | 11/1990 | Guire |
| 4,976,259 A | 12/1990 | Higson et al. |
| 4,979,959 A | 12/1990 | Guire |
| 4,994,043 A | 2/1991 | Ysebaert |

| Patent No. | Date | Inventor(s) |
|---|---|---|
| 5,002,048 A | 3/1991 | Makiej, Jr. |
| 5,002,582 A | 3/1991 | Guire et al. |
| 5,007,419 A | 4/1991 | Weinstein et al. |
| 5,016,024 A | 5/1991 | Lam et al. |
| 5,021,701 A | 6/1991 | Takahashi et al. |
| 5,022,587 A | 6/1991 | Hochstein |
| 5,024,733 A | 6/1991 | Abys et al. |
| 5,046,627 A | 9/1991 | Hansen |
| 5,062,419 A | 11/1991 | Rider |
| 5,063,396 A | 11/1991 | Shiokawa et al. |
| 5,063,922 A | 11/1991 | Hakkinen |
| 5,073,484 A | 12/1991 | Swanson et al. |
| 5,076,266 A | 12/1991 | Babaev |
| 5,080,093 A | 1/1992 | Raabe et al. |
| 5,080,649 A | 1/1992 | Vetter |
| 5,086,765 A | 2/1992 | Levine |
| 5,086,785 A | 2/1992 | Gentile et al. |
| 5,115,803 A | 5/1992 | Sioutas |
| 5,115,971 A | 5/1992 | Greenspan et al. |
| D327,008 S | 6/1992 | Friedman |
| 5,122,116 A | 6/1992 | Kriesel et al. |
| 5,129,579 A | 7/1992 | Conte |
| 5,134,993 A | 8/1992 | Van Der Linden et al. |
| 5,139,016 A | 8/1992 | Waser |
| 5,140,740 A | 8/1992 | Weigelt |
| 5,147,073 A | 9/1992 | Cater |
| 5,152,456 A | 10/1992 | Ross et al. |
| 5,157,372 A | 10/1992 | Langford |
| 5,160,334 A | 11/1992 | Billings et al. |
| 5,164,740 A | 11/1992 | Ivri |
| 5,169,029 A | 12/1992 | Behar et al. |
| 5,170,782 A | 12/1992 | Kocinski |
| 5,180,482 A | 1/1993 | Abys et al. |
| 5,186,164 A | 2/1993 | Raghuprasad |
| 5,186,166 A | 2/1993 | Riggs et al. |
| 5,198,157 A | 3/1993 | Bechet |
| 5,201,322 A | 4/1993 | Henry et al. |
| 5,213,860 A | 5/1993 | Laing |
| 5,217,148 A | 6/1993 | Cater |
| 5,217,492 A | 6/1993 | Guire et al. |
| 5,227,168 A | 7/1993 | Chvapil |
| 5,230,496 A | 7/1993 | Shillington et al. |
| 5,245,995 A | 9/1993 | Sullivan et al. |
| 5,248,087 A | 9/1993 | Dressler |
| 5,258,041 A | 11/1993 | Guire et al. |
| 5,261,601 A | 11/1993 | Ross et al. |
| 5,263,992 A | 11/1993 | Guire |
| 5,279,568 A | 1/1994 | Cater |
| 5,297,734 A | 3/1994 | Toda |
| 5,299,739 A | 4/1994 | Takahashi et al. |
| 5,303,854 A | 4/1994 | Cater |
| 5,309,135 A | 5/1994 | Langford |
| 5,312,281 A | 5/1994 | Takahashi et al. |
| 5,313,955 A | 5/1994 | Rodder |
| 5,319,971 A | 6/1994 | Osswald et al. |
| 5,320,603 A | 6/1994 | Vetter et al. |
| 5,322,057 A | 6/1994 | Raabe et al. |
| 5,342,011 A | 8/1994 | Short |
| 5,342,504 A | 8/1994 | Hirano et al. |
| 5,347,998 A | 9/1994 | Hodson et al. |
| 5,348,189 A | 9/1994 | Cater |
| 5,350,116 A | 9/1994 | Cater |
| 5,355,872 A | 10/1994 | Riggs et al. |
| 5,357,946 A | 10/1994 | Kee et al. |
| 5,372,126 A | 12/1994 | Blau |
| 5,383,906 A | 1/1995 | Burchett et al. |
| 5,388,571 A | 2/1995 | Roberts et al. |
| 5,392,768 A | 2/1995 | Johansson et al. |
| 5,396,883 A | 3/1995 | Knupp et al. |
| 5,414,075 A | 5/1995 | Swan et al. |
| 5,415,161 A | 5/1995 | Ryder |
| 5,419,315 A | 5/1995 | Rubsamen |
| 5,426,458 A | 6/1995 | Wenzel et al. |
| 5,429,122 A | 7/1995 | Zanen et al. |
| 5,431,155 A | 7/1995 | Mareli |
| 5,433,343 A | 7/1995 | Meshberg |
| 5,435,282 A | 7/1995 | Haber et al. |
| 5,435,297 A | 7/1995 | Klein |
| 5,437,267 A | 8/1995 | Weinstein et al. |
| 5,445,141 A | 8/1995 | Kee et al. |
| D362,390 S | 9/1995 | Weiler |
| 5,449,502 A | 9/1995 | Igusa et al. |
| 5,452,711 A | 9/1995 | Gault |
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,542,410 A | 8/1996 | Goodman et al. |
| 5,547,131 A | 8/1996 | Brace |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A | 12/1996 | Salter et al. |
| 5,586,550 A | 12/1996 | Ivri et al. |
| 5,588,166 A | 12/1996 | Burnett |
| 5,601,077 A | 2/1997 | Imbert |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |
| 5,657,926 A | 8/1997 | Toda |
| 5,660,166 A | 8/1997 | Lloyd |
| 5,662,271 A | 9/1997 | Weston et al. |
| 5,664,557 A | 9/1997 | Makiej, Jr. |
| 5,664,706 A | 9/1997 | Cater |
| 5,665,068 A | 9/1997 | Takamura |
| 5,666,946 A | 9/1997 | Langenback |
| 5,670,999 A | 9/1997 | Takeuchi et al. |
| 5,685,491 A | 11/1997 | Marks et al. |
| 5,692,644 A | 12/1997 | Gueret |
| 5,694,920 A * | 12/1997 | Abrams et al. ........... 128/200.16 |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,730,629 A | 3/1998 | Samejima et al. |
| 5,744,515 A | 4/1998 | Clapper |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |
| 5,790,151 A | 8/1998 | Mills |
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,862,802 A | 1/1999 | Bird |

| | | |
|---|---|---|
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,916,524 A | 6/1999 | Tisone |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,000,396 A | 12/1999 | Melker et al. |
| 6,007,518 A | 12/1999 | Kriesel et al. |
| 6,012,450 A | 1/2000 | Rubsamen |
| 6,014,970 A | 1/2000 | Ivri et al. |
| 6,026,809 A | 2/2000 | Abrams et al. |
| 6,029,666 A | 2/2000 | Aloy et al. |
| 6,032,665 A | 3/2000 | Psaros |
| 6,037,587 A | 3/2000 | Dowell et al. |
| 6,039,696 A | 3/2000 | Bell |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,090,080 A | 7/2000 | Jost et al. |
| 6,096,011 A | 8/2000 | Trombley, III et al. |
| 6,105,877 A | 8/2000 | Coffee |
| 6,106,501 A | 8/2000 | Michel |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,269,810 B1 | 8/2001 | Brooker et al. |
| 6,270,473 B1 | 8/2001 | Schwebel |
| 6,273,342 B1 | 8/2001 | Terada et al. |
| 6,280,421 B1 | 8/2001 | Kirchhofer et al. |
| 6,318,640 B1 | 11/2001 | Coffee |
| 6,328,030 B1 | 12/2001 | Kidwell et al. |
| 6,328,033 B1 * | 12/2001 | Avrahami ............... 128/203.15 |
| 6,341,732 B1 | 1/2002 | Martin et al. |
| 6,358,058 B1 | 3/2002 | Strupat et al. |
| 6,367,470 B1 | 4/2002 | Denyer et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,530,370 B1 | 3/2003 | Heinonen |
| 6,540,153 B1 | 4/2003 | Ivri |

| | | |
|---|---|---|
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,581,595 B1 | 6/2003 | Murdock et al. |
| 6,595,208 B1 | 7/2003 | Coffee et al. |
| 6,598,602 B1 | 7/2003 | Sjoholm |
| 6,615,824 B2 | 9/2003 | Power |
| 6,629,646 B1 | 10/2003 | Ivri |
| 6,640,804 B2 | 11/2003 | Ivri |
| 6,651,650 B1 | 11/2003 | Yamamoto et al. |
| 6,705,315 B2 | 3/2004 | Sullivan et al. |
| 6,732,944 B2 | 5/2004 | Litherland et al. |
| 6,745,768 B2 | 6/2004 | Colla et al. |
| 6,745,770 B2 | 6/2004 | McAuliffe et al. |
| 6,755,189 B2 | 6/2004 | Ivri et al. |
| 6,769,626 B1 | 8/2004 | Haveri |
| 6,782,886 B2 | 8/2004 | Narayan et al. |
| 6,810,876 B2 | 11/2004 | Berthon-Jones |
| 6,814,071 B2 | 11/2004 | Klimowicz et al. |
| 6,817,361 B2 | 11/2004 | Berthon-Jones et al. |
| 6,840,240 B1 | 1/2005 | Berthon-Jones et al. |
| 6,845,770 B2 | 1/2005 | Klimowicz et al. |
| 6,851,626 B2 | 2/2005 | Patel et al. |
| 6,860,268 B2 | 3/2005 | Bohn et al. |
| 7,360,536 B2 * | 4/2008 | Patel et al. ................ 128/200.14 |
| 2001/0013554 A1 | 8/2001 | Borland et al. |
| 2001/0015737 A1 | 8/2001 | Truninger et al. |
| 2002/0011247 A1 | 1/2002 | Ivri et al. |
| 2002/0023639 A1 * | 2/2002 | Ivri et al. ................. 128/200.16 |
| 2002/0023650 A1 | 2/2002 | Gunaratnam et al. |
| 2002/0033178 A1 | 3/2002 | Farrell et al. |
| 2002/0036601 A1 | 3/2002 | Puckeridge et al. |
| 2002/0078958 A1 | 6/2002 | Stenzler |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2002/0185125 A1 * | 12/2002 | Klimowicz et al. ...... 128/200.16 |
| 2003/0019493 A1 | 1/2003 | Narayan et al. |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |
| 2004/0035413 A1 | 2/2004 | Smaldone et al. |
| 2004/0035490 A1 | 2/2004 | Power |
| 2004/0050947 A1 | 3/2004 | Power et al. |
| 2004/0134494 A1 | 7/2004 | Papania et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0194783 A1 | 10/2004 | McAuliffe et al. |
| 2004/0226561 A1 | 11/2004 | Colla et al. |
| 2004/0226566 A1 | 11/2004 | Gunaratnam et al. |
| 2004/0256488 A1 | 12/2004 | Loeffler et al. |
| 2005/0011514 A1 | 1/2005 | Power et al. |
| 2005/0113795 A1 | 5/2005 | Ott et al. |
| 2006/0292304 A1 | 12/2006 | Tisone |

FOREIGN PATENT DOCUMENTS

| | | |
|---|---|---|
| DE | 11 03 522 | 3/1964 |
| EP | 973 458 | 10/1964 |
| EP | 0 049 636 | 4/1982 |
| EP | 0 103 161 | 3/1984 |
| EP | 0 134 847 | 3/1985 |
| EP | 0 178 925 | 4/1986 |
| EP | 0 387 222 | 9/1990 |
| EP | 0 432 992 | 6/1991 |
| EP | 0 476 991 | 3/1992 |
| EP | 0 480 615 | 4/1992 |
| EP | 0 510 648 | 10/1992 |

| | | |
|---|---|---|
| EP | 0 516 565 | 12/1992 |
| EP | 0 542 723 | 5/1993 |
| EP | 0739654 | 10/1996 |
| EP | 0 933 138 | 4/1999 |
| EP | 0 923 957 | 6/1999 |
| EP | 1 142 600 | 10/2001 |
| GB | 973 458 | 10/1964 |
| GB | 1 454 597 | 11/1976 |
| GB | 2 073 616 | 10/1981 |
| GB | 2 101 500 | 1/1983 |
| GB | 2 177 623 | 1/1987 |
| GB | 2 240 494 | 7/1991 |
| GB | 2 272 389 | 5/1994 |
| JP | 51106779 | 9/1976 |
| JP | 57-023852 | 2/1982 |
| JP | 57-105608 | 7/1982 |
| JP | 58-061857 | 4/1983 |
| JP | 58-139757 | 8/1983 |
| JP | 59-142163 | 8/1984 |
| JP | 60-004714 | 1/1985 |
| JP | 61-008357 | 1/1986 |
| JP | 61-215059 | 9/1986 |
| JP | 02-135169 | 5/1990 |
| JP | 02-189161 | 7/1990 |
| JP | 60-07721 | 1/1994 |
| WO | WO 82/03548 | 10/1982 |
| WO | WO 92/07600 | 5/1992 |
| WO | WO 92/11050 | 9/1992 |
| WO | WO 92/17231 | 10/1992 |
| WO | WO 93/01404 | 1/1993 |
| WO | WO 93/10910 | 6/1993 |
| WO | WO 94/09912 | 5/1994 |
| WO | WO 96/09229 | 3/1996 |
| WO | WO9907478 | 2/1999 |
| WO | WO 99/17888 | 4/1999 |
| WO | WO 9963946 | 12/1999 |
| WO | WO 00/37132 | 6/2000 |
| WO | WO 0151110 | 7/2001 |
| WO | WO 03057291 | 7/2003 |

OTHER PUBLICATIONS

Allen, "Particle Size Measurement", Third Edition, Chapman and Hall, pp. 167-169, (1981).
Ashgriz, et al., "Development of a Controlled Spray Generator", Rev. Sci. Instrum., pp. 1291-1296, vol. 58, No. 7, (1987).
Berggren, "Pilot Study of Nebulized Surfactant Therapy for Neonatal Respiratory Distress Syndrome", Acta Paediatr 89: 460-464, Taylor & Francis, ISSN 0803-5253, Sweden, (2000).
Berglund, et al., "Generation of Monodisperse Aerosol Standards", Environ. Sci. Tech,, pp. 147-153, vol. 7, No. 2, (Feb. 1973).
Cipolla, et al., "Assessment of Aerosol Delivery Systems for Recombinant Human Deoxyribonuclease", S.T.P. Pharma Sciences, 4 (1), 50-62, (1994).
Cippola, et al., "Characterization of Aerosols of Human Recombinant Deoxyribonuclease I (rhDNase) Generated by Neulizers", Pharm. Research II, (4), pp. 491-498, (1994).
Dogan, Thesis: "Flexional Moonie and Cymbal' Actuators", Penn State University, (1994).
Duarte, et al., "Inhalation Therapy During Mechanical Ventilation", Rasp. Care Clinics of North America, Aerosol Therapy, pp. 233-259, vol. 7, No. 2, (Jun. 2001).
Fink, at al., "Aerosol Drug Therapy", Clinical Practice in Respiratory Care, Chapter 12, pp. 308-342, (1999).

Fink, at al., "Aerosol Therapy in Mechanically Ventilated Patients: Recent Advances and New Techniques", Seminars in Respiratory and Critical Care Medicine, pp. 133-201, vol. 21, No. 3, (2000).
Fink, et al., "Diagram from and abstract of article entitled Optimizing efficiency of nebulizers during mechanical ventilation: the effect of placement and type of ventilator circuit," Chest, pp. 116:312S, (1999).
Gaiser Tool Company Catalog, pp. 26, 29-30, (1990).
Gonda, "Therapeutic Aerosols," Pharmaceutics, The Science of Dosage Form Design, Editor: M.E. Aulton, pp. 341-358, (1988).
Hancock, et al, "Molecular Mobility of Amorphous Pharmaceutical Solids Below Their Glass Transition Temperature," Pharmaceutical Research, 12, pp. 799-806, (1995).
Heyder, et al., "Deposition on particles in the human respiratory tract in the size range 0.005-15 microns," J. Aerosol Sci., 17, pp. 811-825, (1986).
Hickey, "Pharmaceutical Inhalation Aerosol Technology," Drugs And The Pharmaceutical Science, vol. 54, pp. 172-173, (1992).
Hikayama, et al., "Ultrasonic Atomizer with Pump Function," Tech. Rpt. IEICE, Japan, US88-74:25, Figures only, (1988).
Jorch, Letter to the Editor: "Surfactant Aerosol Treatment of Respiratory Distress Syndrome in Spontaneously Breathing Premature Infants," Pediatric Pulmonology, Wiley-Liss, 24, pp. 222-224, (1997).
Maehara, et al., "Atomizing rate control of a multi-pinhole-plate ultrasonic atomizer," J. Acoustical Soc. Japan, vol. 44,No. 2, pp. 116-121, (1988).
Maehara, et al, "Influence of the vibrating system of a multipinhole-plate ultrasonic nebulizer on its performance," Review of Scientific Instruments. vol. 57, No. 1, pp. 2870-2876, (Nov. 1986).
Maehara, et al., "Influences of liquid's physical properties on the characteristics of a multi-pinhole-plate ultrasonic atomizer," J. Acoustical Soc., Japan, vol. 44, No. 6, pp. 425-431, (1988).
Maehara, et al., "Optimum Design Procedure for Multi-Pinhole-Plate Ultrasonic Atomizer," Japanese Journal of Applied Physics, vol. 26, Supplement 26-1, pp. 215-217, (1987).
Nogi, et al., "Mixture Formation of Fuel Injection System in Gasoline Engine," Nippon Kikai Gakkai Zenkoku Taikal Koenkai Kocn Ronbunshu, 69, pp. 660-662, Figures only, (1991).
Palls Tech Pd an Pd Alloy Process—Procedures for the Analysis of Additive IVS in Palls Tech Plating Solutions by HPLC, Technical Bulletin, Electroplating Chemicals & Services, 029-A, Lucent Technologies, pp. 1-5, (1996).
Siemens, "Servo Ultra Nebulizer 345 Operating Manual," pp. 1-23.
Smaldone, "Aerosolized Antibiotics: Current and Future," Respiratory Care, vol. 54, No. 6, pp. 667-675, (2000).
Smedsass-Lofvenbert, "Nebulization of Drugs in a Nasal CPAP System," Scandinavian University Press, Acta Paediatr, Sweden, 88, pp. 89-92, (1999).
TSI Incorporated product catalog. "Vibrating Orifice Aerosol Generator," (1989).
Ueha, et al., "Mechanism of Ultrasonic Atomization Using a Multi-Pinhole Plate," J. Accoust. Soc. Jpn., (E)6,1, pp. 21-26, (1985).
Wehl, "Ink-Jet Printing: The Present State of the Art ," for Siemens AG, (1989).
Abys JA et al "Annealing Behavior of Palladium-Nickel Alloy Electrodeposits" Plating and Surface Finishing, p. 1-7 (1996).
US 5,954,699, 09/1999, Jost et al. (withdrawn)

* cited by examiner

Fig. 1

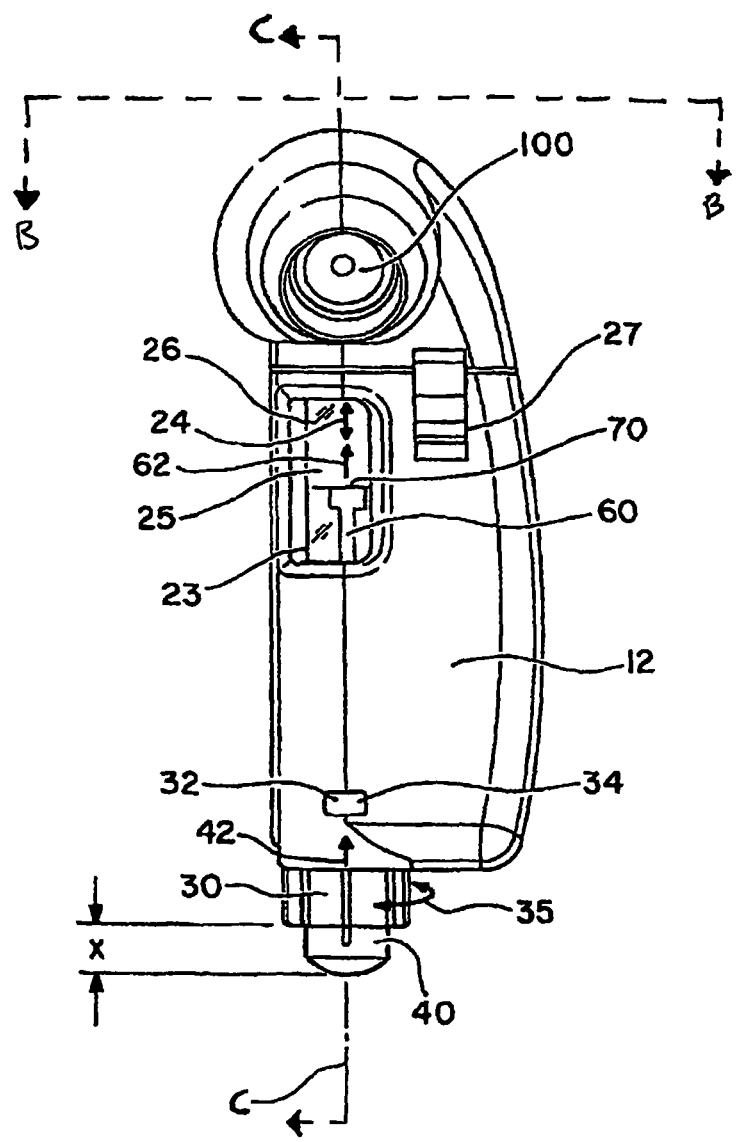

200 — SELECTION OF A DOSE BY OPERATION OF A DOSE MECHANISM

210 — OPERATION OF A SCREW MECHANISM, BASED ON THE SELECTION OF THE DOSE MECHANISM, TO SET A DISTANCE OF TRAVEL OF A PLUNGER

220 — OPERATION OF AN ACTUATOR TO MOVE THE PLUNGER ACCORDING TO THE DISTANCE SET BY THE SCREW MECHANISM

230 — DISPLACEMENT OF FLUID, BY ACTION OF THE PLUNGER MOVING THE SET DISTANCE, FROM A VIAL INTO A RESERVOIR

240 — OPERATION OF AN AEROSOL GENERATOR THAT IS IN FLUID COMMUNICATION WITH THE RESERVOIR

250 — AEROSOLIZATION OF THE FLUID

*Fig. 3*

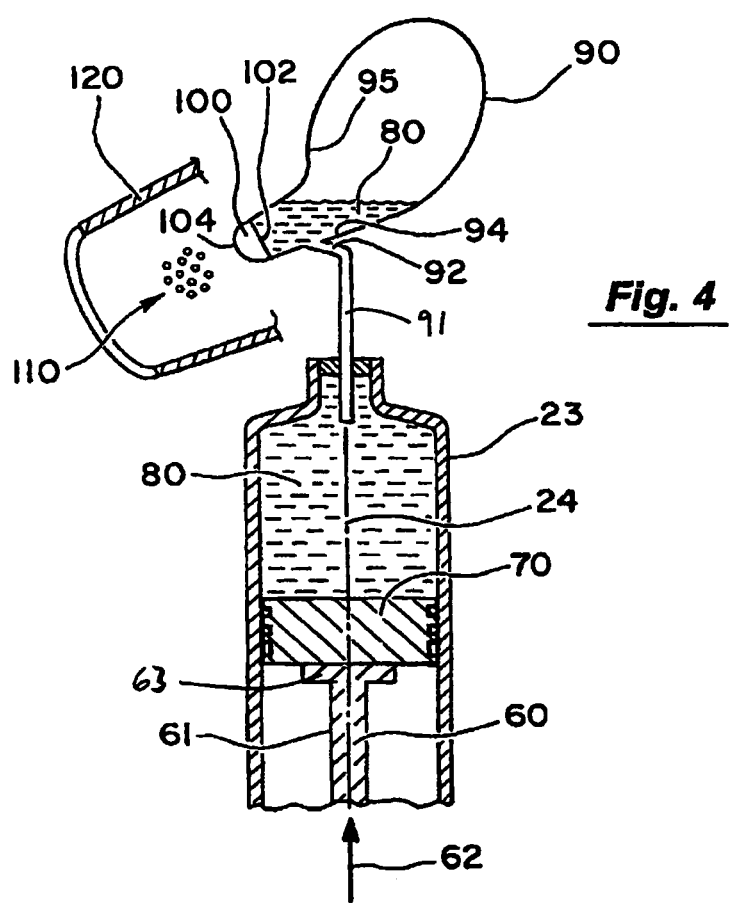
Fig. 4
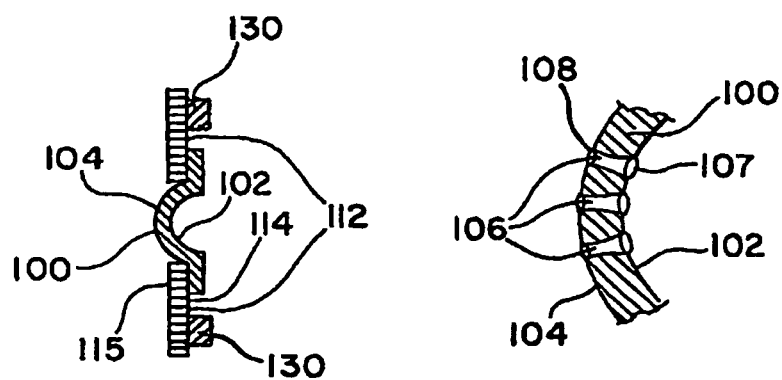
Fig. 5A  Fig. 5B

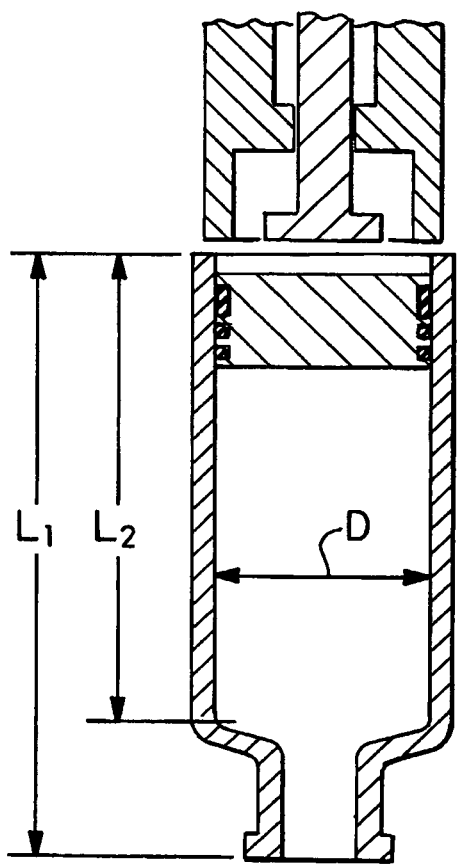 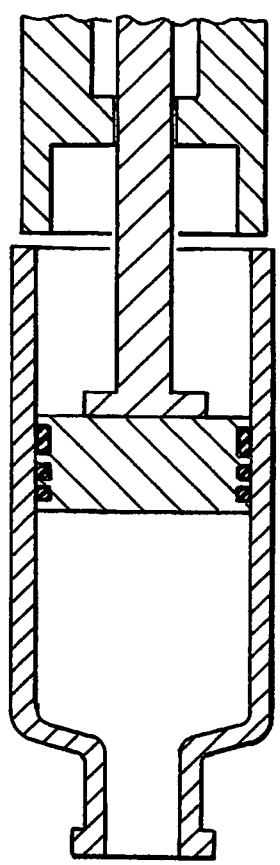
*Fig. 7A*                    *Fig. 7B*

DEVICES AND METHODS FOR NEBULIZING FLUIDS FOR INHALATION

CROSS-REFERENCES TO RELATED APPLICATIONS

This application is a divisional application of U.S. patent application Ser. No. 10/338,194, filed on Jan. 7, 2003, now U.S. Pat. No. 7,360,536, which claims the benefit of U.S. Provisional Application No. 60/403,454, filed on Aug. 13, 2002, and U.S. Provisional Application No. 60/346,789, filed on Jan. 7, 2002, the complete disclosure of which is hereby incorporated herein by reference.

BACKGROUND OF THE INVENTION

The present invention is directed to the field of methods and devices for nebulizing fluids. In particular, the present invention is directed to methods and devices by which a user may select a dose of medication from a multi-dose vial and nebulize the selected dose for inhalation.

BRIEF SUMMARY OF THE INVENTION

The present invention provides a nebulizing device that is preferably a hand-held nebulizing device for inhalation of the nebulized fluid. The device has a nebulizing element and a mouthpiece through which the user inhales the nebulized fluid. The nebulizing element, which may interchangeably be referred to as an aerosolization element, may be a vibrating element with holes through which the fluid is ejected as a mist, although other suitable nebulizing elements may be used without departing from the present invention.

The fluid is held in a container that holds a number of doses of the fluid. The container delivers the fluid to a reservoir. A plunger acts on the container to cause fluid to flow from the container into the reservoir. A screw mechanism controls the distance of travel of the plunger. A dosing mechanism allows a user to select a particular dose to be administered by inhalation, and the dosing mechanism cooperates with the screw mechanism to set a distance of travel of the plunger that corresponds to the dose selected by the user. The dosing mechanism may rotate within a plane. An actuation mechanism is operated by the user to carry out the actual movement of the plunger according to the distance of travel set by the dosing mechanism. In this manner, a user can verify the amount of fluid selected for aerosolization before that amount of fluid is moved into the reservoir for aerosolization. If a user sees that the dose amount needs to be modified, the user can do so by further operation of the dosing mechanism before any fluid is actually released from the container. In this manner, an inadvertent selection of a dose will not result in loss of that amount of fluid, because the user has the opportunity to verify and if called for readjust the selection before fluid is moved from the container into the reservoir.

The actuator will typically travel in a direction perpendicular to the plane of rotation of the dosing mechanism. In this manner, dosing can be done easily and accurately by the user with a simple rotation action prior to attempting to deliver the dosed amount into a reservoir for aerosolization. The actuation can be done simply, in a discrete manner, prior to or while the user has oriented the device for inhalation through the mouthpiece of the device. In addition, the actuation mechanism is configured so that a single, predetermined movement of the actuation mechanism causes the plunger to travel the entire distance that a user selects, regardless of the particular distance of travel chosen by the user. Thus, delivery of the fluid from the container to the reservoir for aerosolization may be carried out by a single motion by the user operating the actuation mechanism, thus reducing encumbering maneuvering that could be required in delivering a particular amount of fluid from the container to the reservoir. This contributes to ease of operation of the nebulizer, and thus improves the level of care that a user may administer in using the nebulizer. In some cases, a patient may not comply with a particular drug regimen because it is perceived as inconvenient or embarrassing, as might be the case with injunctions or cumbersome inhalation devices. Accordingly, the present invention minimizes such potential non-compliance factors because the user may dial a dose out of the line of sight of others, the user may operate the actuator with a simple button press, and the user needs only a single hand to bring the nebulizer to the mouth.

BRIEF DESCRIPTION OF THE DRAWINGS

Embodiments of the invention will be described in greater detail below with reference to the drawings.

FIG. 1 is schematic representation of a partial exploded side view of a nebulizer embodiment according to the present invention.

FIG. 2 is a perspective view of the nebulizer of FIG. 1.

FIG. 3 is a flow chart showing a method and steps in accordance with the present invention.

FIG. 4 is a cutaway cross-sectional view along axis A of the device as depicted in FIG. 2 and in accordance with the present invention.

FIG. 5A is a detail cross-section view of the nebulizer of FIG. 1 taken along line A-A.

FIG. 5B is a detail cross-section view of the nebulizer of FIG. 1 taken along line A-A.

FIGS. 7A and 7B are detail cross-sectional cutaway views of the nebulizer depicted in FIG. 2 taken along line C-C.

DETAILED DESCRIPTION OF THE INVENTION

Figure 1:
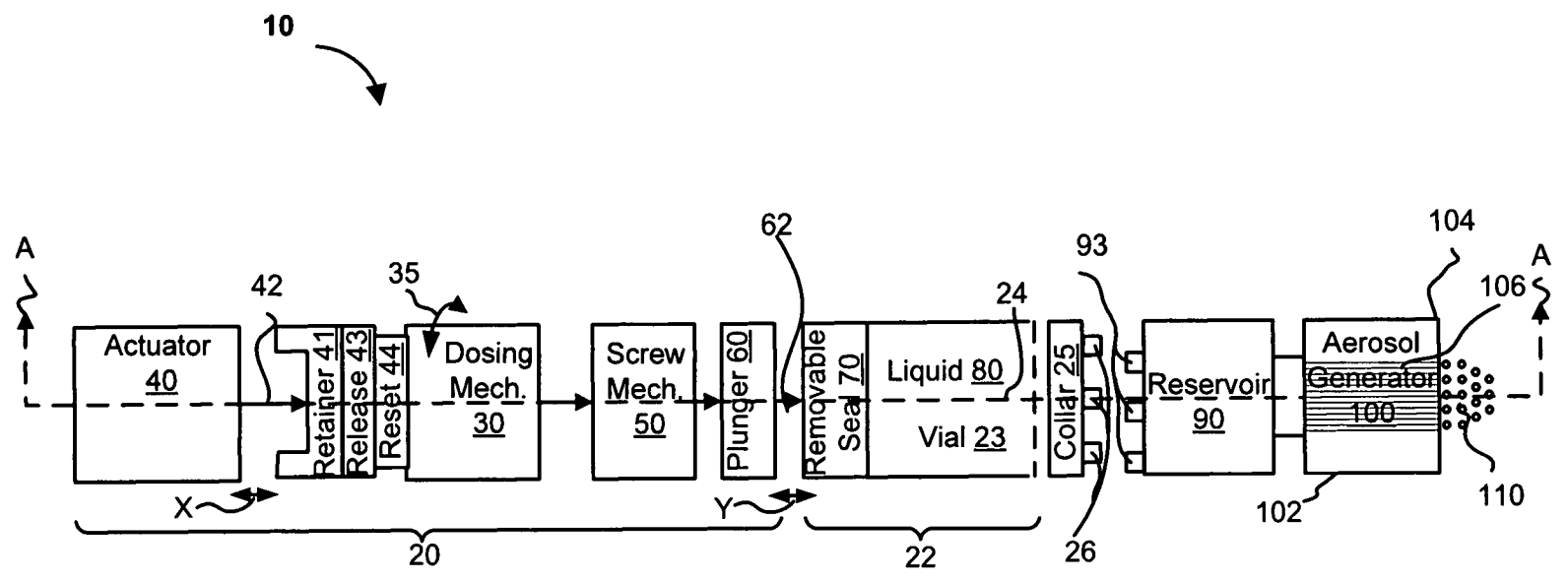
Figure 6:
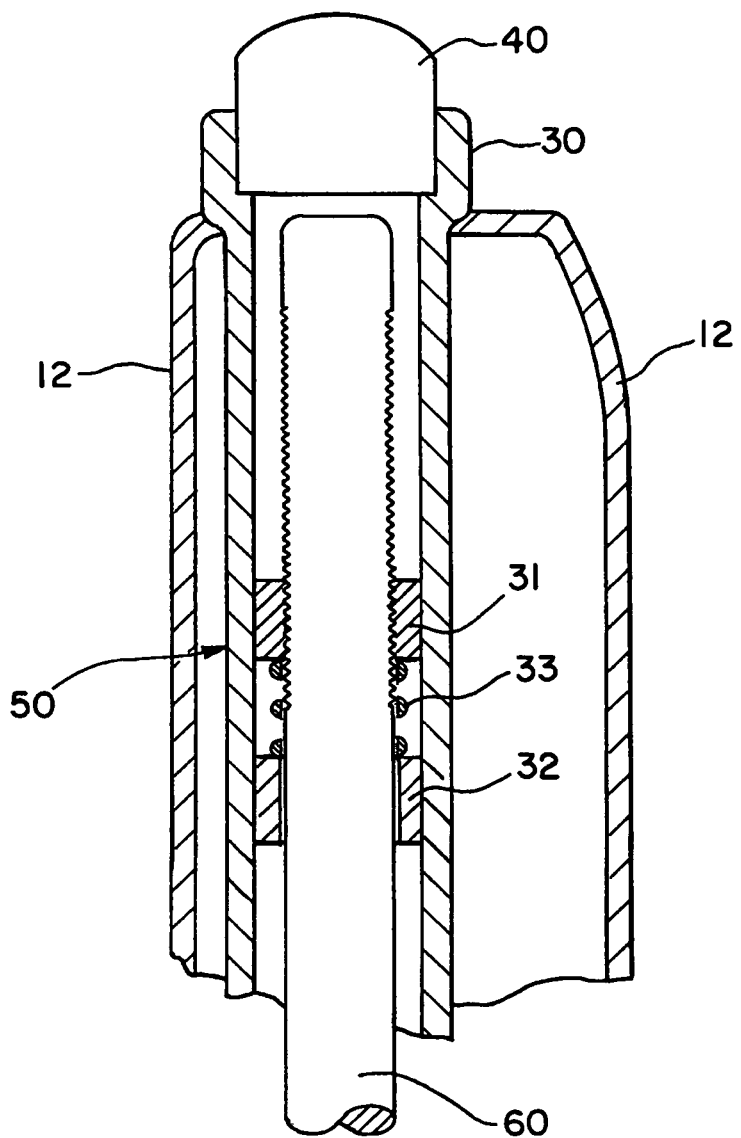
FIG. 6 is a detail cross-sectional cutaway view of the nebulizer of FIG. 2 taken along line B-B.

Referring to FIG. 1, a nebulizing inhaler according to the present invention is represented schematically. The device 10 comprises a titration mechanism 20, a vial mechanism 22, a reservoir 90 and an aerosol generator 100. The titration mechanism comprises a titration control mechanism, which may be referred to a dosing mechanism 30, a screw mechanism 50, a plunger 60, an actuator 40, a retainer 41, a release mechanism 43, and a reset mechanism 44. The plunger is configured to travel to and fro, as explained in further detail below, in the direction of arrow 62 (this being the "to" motion, the "fro" motion being the reverse thereof). Accordingly, and as depicted in FIG. 1, arrow 62 defines the axis of travel of the plunger 60. The actuator is configured to travel to and fro, as explained in further detail below, in the direction of the arrow 42 (this being the "to" motion, the "fro" motion being the reverse thereof). Accordingly, and as depicted in FIG. 1, the arrow 42 defines the longitudinal axis of travel of the actuator 40. The axis of travel of the actuator 40 is also represented as the broken line A in FIG. 2. The retainer 41 is employed to releasably capture the actuator 40 when the actuator 40 is fully moved a distance from an initial position to a predetermined actuation position. The release mechanism 43 releases the retainer 41 to allow the actuator 40 to return to the initial position from the predetermined actuation position. The release mechanism 43 and the reset mechanism 44 are linked together such that the release mechanism 43 causes the reset mechanism 44 to reset a visual indictor.

The vial mechanism 22 comprises a container, such as a vial 23 that defines a central longitudinal axis 24 and movable seal 70 movably captured in the vial 23. The moveable seal 70 is movable along the central axis 24 of the vial 23 by action of plunger 60 upon the moveable seal 70 in the direction of arrow 62. A liquid 80 is provided in the vial mechanism 22. The liquid 80 is moved into a reservoir 90 by action of the movable seal 70 against the liquid 80, as the moveable seal is moved, in the direction of arrow 62, by action of the plunger in the direction of arrow 62, upon the moveable seal 70. Once the liquid is in the reservoir 90, the liquid 80 can be nebulized for inhalation by a user.

Upon exhaustion of liquid from the vial, the vial may be removed and replaced as necessary with a new vial containing liquid, thus putting the nebulizer in a state ready for operation. The vial 23 may be of a transparent material, such as glass, and thus the level of fluid 80 within it can readily be seen. The level of fluid in the vial 23 can be seen through window 25 in the device 10 (see FIG. 2).

Liquid in the reservoir may be nebulized by an aerosolization element 100 (FIG. 1). The aerosolization element may comprise a first face 102 that faces into the reservoir and a second face 104 that is directed to a mouthpiece. The aerosolization element may have a plurality of apertures 106 extending through from the first face 102 to the second face 104 (see FIGS. 5A and 5B). Liquid on the reservoir side of the aerosolization element may be drawn through the apertures and emitted, as an aerosolized mist 110, from the other. For example, the liquid may be drawn through the apertures by vibratory motion of the element. The apertures of the element may be tapered. The taper may have a wider portion 107 toward the reservoir and narrower portion 108 away from the reservoir and toward the mouthpiece (FIG. 5B). The aerosolization element may be non-planar, and may be concave. The concave side may be positioned toward the reservoir 90. The side emitting the aerosolized mist 100 may be convex. Other configurations of moving fluid from the reservoir through the aerosolization element and emitting the fluid as a mist therefrom may be employed without departing from the present invention.

When a new vial assembly is needed, the device 10 may be opened by operation of latch assembly 27, thus allowing removal of a spent vial assembly or vial and replacement thereof. The reservoir 90 may also be removed and replaced by opening the device 10 by operation of latch assembly 27. The vial assembly 22 may be linked to the reservoir 90 in such a manner that one cannot be removed from the other without breakage to one or both of these components. The vial assembly 22 may have a collar 25 with one or more tabs 26, and the reservoir 90 may have one or more detents 93 that can interlock with the tabs 26. In this manner, the tabs 26 and detents 93 may hold the vial assembly 22 and the reservoir 90 together and prevent their disassembly from each other. With the vial assembly 22 and the reservoir 90 being assembled in such a manner, inadvertent use of the vial for purposes other than use with the nebulizer, such as injection, can be avoided, as the concentration of drug within the liquid may be far greater for inhalation than the concentration of the same drug in a liquid for injection. In this manner, both the vial assembly 22 and the reservoir 90 may need to be removed and replaced as a tandem assembly. The present invention is embodied in the nebulizer described herein without one or both of the vial assembly 22 and the reservoir 90, as these subassembly components are likely to be removed and reassembled to each other and back into the nebulizer. Removable vial assemblies and removable reservoirs are described in co-assigned and co-pending application Ser. No. 10/043,075 which is hereby incorporated herein in its entirety. The present invention is also embodied in the nebulizer described herein comprising the vial assembly and the reservoir, as well as in methods of nebulizing liquid comprising providing a vial assembly and a reservoir. The present invention is also embodied in methods of nebulizing liquid comprising inserting the vial assembly in to a nebulizer and comprising inserting a reservoir into a nebulizer.

The vial mechanism 22 may be received within the device 10 to align with the titration mechanism such that the direction of travel of the actuator 40, the direction of travel of the plunger 60 and the direction of travel of the movable seal 70 in the vial 23 are all substantially parallel. The vial mechanism 22 may be received within the device 10 to align with the titration mechanism in a substantially coaxial manner, such that the action of the actuator 40, the plunger 60 and the movable seal 70 in the vial 23 are all substantially coaxial. Thus, when the vial mechanism 22 is placed within the device 10 the central axis 24 of the vial 23, and thus the axis of movement of the movable seal 70, which is captured within the vial 23, the axis of travel of the plunger 60, and the axis of travel of the actuator 40 may be substantially parallel and may be coaxial (see FIGS. 1, 2 and 4). The dosing mechanism 30 defines an axis of rotation, and this axis may be and preferably is coaxial with the longitudinal axis of the vial 23 when the vial mechanism is placed in the nebulizer. Accordingly, the axis of rotation of the dosing mechanism, the longitudinal axis of the vial and the axis of travel of the plunger are all coaxial. An object of the present invention is a nebulizer of an overall longitudinal dimension (substantially parallel to the longitudinal axis of the vial) that will essentially fit in the hand of a user and be used substantially inconspicuously to increase user compliance with a chosen administration regimen (FIG. 2). Similarly, an object of the present invention is a nebulizer that can fit easily in a garment pocket or a small bag. In order to fit a sufficient quantity of fluid in the vial, for example, a week's supply of insulin, while maintaining these size dimension considerations and accommodating the reservoir, mouthpiece and other components of the nebulizer, the present invention, in one embodiment, resides in a nebulizer having a vial of unconventional dimension with respect to vials typically used in injection devices. Accordingly, in one embodiment, the nebulizer of the present invention has a vial assembly with a vial having a ratio of the internal diameter D, in the portion where the movable seal can travel, to the overall length $L_1$ of the vial (FIG. 7A), for example, in the range of about 1:3.5 to about 1:4.5, or between about 1:3.7 to about 1:4.2. Similarly, the ratio may be between about 1:3.8 to about 1:4.0. The ratio may be about 1:3.9 For example, the vial may have a diameter of about 12 mm and a length of about 47 mm. Likewise, the vial may have a diameter of about 12.0 mm and a length of about 46.8 mm. Alternatively, the measurement of vial length can be taken as the length of the effective volume of the vial $L_2$ (FIG. 7A), the effective volume including only the portion of the vial in which moveable seal can occupy (as opposed to the narrowing neck), and thus the ratio of vial diameter to length of the effective volume may be between about 1:3.0 and abut 1:3.8, or between about 1:3.2 to about 1:3.6, or between 1:3.3 to about 1:3.5, or about 1:3.4. For example, this length may be about 38 mm, or this length may be about 37.7 mm.

In operation, a user operates the dosing mechanism 30 to select a particular dose amount that the user desires to have nebulized for inhalation. The dosing mechanism acts upon the screw mechanism 50. The screw mechanism 50 is linked to the plunger 60. The actuator 40 is linked to the screw mechanism 50 so that linear movement of the actuator 40 in the direction of arrow 42 causes linear movement of the plunger 60 in the direction of arrow 62.

There is, however, no actual movement of the plunger 60 against the moveable seal by operation of the dose mechanism 30; rather, operation of the dose control 30 only sets the distance that the plunger will be able to travel in the subsequent stroke of the actuator 40. Thus, if a user in advertently selects an incorrect dose, the user may readjust the dosing mechanism 30 for the desired amount of drug without wasting the previous incorrectly selected dose amount. In this manner, the user may select a dose to be nebulized, and after verification correct this dose if that is necessary, before nebulization begins. Once the user has determined and selected the correct dose amount by operation of dosing mechanism 30, the user presses the actuator 40 in the direction of arrow 42. The pressing action of the actuator 40 acts upon the screw mechanism 50, which then moves the plunger 60 in the direction of arrow 62. The distance that the plunger 60 travels, in the direction of arrow 62, is controlled by the screw mechanism 50 according to the selected dose amount based on the user's operation of the dosing mechanism 30. In this manner, when the user is ready to commence inhalation, after discreetly selecting a dose, the user may bring the device to the user's mouth and at this point press the actuator 40 with a single button press motion to deliver medication to the reservoir for nebulization. Alternatively, the user may select the dose and operate the actuator to deliver the dose into the reservoir prior to raising the nebulizer to the user's mouth. Discreet dosing and delivery is an important feature of the present invention, because it increases user compliance with a prescribed regimen. Certain drugs, such as insulin, require administration during the course of a day, perhaps in conjunction with meals; thus a user may be forced to take a dose in a public setting. In some cases, a user will not comply with a drug regimen because it is perceived as inconvenient or embarrassing. Accordingly, the present invention minimizes such potential non-compliance factors—the user may dial a dose out of the line of sight of others, the user may operate the actuator with a simple button press, and the user needs only a single hand to bring the nebulizer to the mouth.

Accordingly, the actuator 40 is configured to travel a fixed distance X (see FIGS. 1 and 2) and the screw mechanism 50 permits the plunger 60 to travel a variable distance Y (see FIG. 1), based on the dose amount selected by operation of the dosing mechanism 30. The specific distances of travel for the plunger 60 according to dose amounts selected by operation of the dosing mechanism 30 may be determined based upon interior diameter of the vial 23.

Screw mechanisms such as screw mechanism 50, that selectively control the linear distance a plunger may travel, based on a selected setting of a dosing mechanism, with such travel being carried out by a user moving an actuator a fixed distance, are known, for example, in injection pens used by diabetics to selectively inject a chosen amount of insulin. Such injection pens are widely available, for example, from Disetronic Medical Systems, AG, Burgdorf, Switzerland. Such pens and are described in the art, as for example, U.S. Pat. Nos. 4,883,472; 5,730,629; 6,090,080; 6,106,501; 6,280,421 and 5,954,699, the entire contents of which are hereby incorporated herein by reference.

When the plunger travels a variable distance Y according the dose amount selected by a user in first operating the dosing mechanism 30 and then operating the actuator 40, it acts upon the movable seal 70. The movable seal 70 moves within the vial 23 to displace an amount of liquid 80 from the vial 23 into the reservoir 90. The reservoir 90 is in fluid communication with an aerosol generator 100, so that liquid displaced from the vial 23 into the reservoir 90, upon operation of the aerosol generator 100, is emitted from the device as fine droplets that form a mist 110.

With reference to FIG. 2 the device 10 comprises a housing 12. The dosing mechanism 30 is rotatably attached to the housing 12. The dosing mechanism rotates circularly in a plane as shown by arrow 35 (FIGS. 1 and 2). Rotation of the dosing mechanism 30 causes operation of the screw assembly (see FIG. 1). An indicator 32 displays selectable dose amounts based on rotation of the dosing mechanism 30 by a user, so that a user may select a displayed dose amount by rotating the dosing mechanism 30. Once a user has determined that the selected dose amount is correct, the user presses actuator 40 in the direction of arrow 42. The to and fro (i.e. forward and reverse) directions of travel of the actuator 40 may be substantially perpendicular to the plane of rotation of the dosing mechanism 30 (see FIGS. 1 and 2). The motion of the actuator 40 in the direction of the arrow 42 moves the selected dose amount of medication into the reservoir (see FIG. 1), so that operation of the aerosol generator 100 causes the fluid to be ejected from the device as a mist 110 (see FIG. 1).

Referring now to FIG. 3, a flow chart of steps according to the present invention is shown. Step 200 is the selection of a dose by operation of a dose mechanism. Step 210 is the operation of a screw mechanism, based on the selection of the dose mechanism, to set a distance of travel of a plunger. Step 220 is the operation of an actuator to move the plunger according to the distance set by the screw mechanism. Step 230 is the displacement of fluid, by action of the plunger moving the set distance, from a vial into a reservoir. Step 240 is the operation of an aerosol generator that is in fluid communication with the reservoir. Step 250 is the aerosolization of the fluid.

Referring again to FIG. 2, the window 25 may be covered with a transparent pane 26. The window 25, and thus the transparent pane 26, may have a curvature for better viewing of the vial 23 which may be substantially cylindrical. The indicator 32 comprising a displayed dose 34 so that a user may see the dose selected prior to pushing the actuator 40. The dosing mechanism 30 has a circular motion as shown by arrow 35. The circular motion of the dosing mechanism, as shown by arrow 35, is substantially perpendicular to the axis of travel of the actuator 40.

Referring to FIG. 4, a reservoir 90 receives the liquid that is displaced from the vial 23 upon actuation of the plunger 60. The liquid may travel from the vial 23 to the reservoir 90 through a cannula 91. The reservoir may have a channel such as a delivery tube 92 and a lumen 94, which lumen may be defined by a wall 95. The liquid may flow from the vial 23 through the cannula 91 and then through the delivery tube 92 into the lumen 94. The reservoir is in fluid communication with an aerosolizing element 100 as described above. The first face 102 of the aerosolizing element 100 may be contiguous with the reservoir, so that fluid in the reservoir will abut the first face of the aerosolizing element. In this manner, a wide range of dosages of liquid may be placed within the reservoir by the user carrying out the single actuation motion; for example, the dose moved into the reservoir may be 30 microliters or, alternatively, for example, the dose moved into the reservoir may be 250 microliters. By placing the entirety of the liquid to be aerosolized in the reservoir at once, uninterrupted aerosolization may be carried out smoothly, without inconsistencies that might occur if liquid were to be provided to the aerosolization element other than as a single bolus, such as, for example, by a drop-by-drop delivery, or if other modes of aerosolization are used, such as ultrasonic or jet nebulizers, both of which apply energy or force directly to the liquid. By creating aerosol from the liquid by vibration of an apertured aerosolization element, less potential degradation of the drug and far greater aerosol particle size control can be achieved, and likewise better dose accuracy can be achieved. The second face of the aerosolization element is positioned such that aerosol emanating from it may be drawn through a mouthpiece 120 of the nebulizer 10. The fluid is delivered into the reservoir in such a manner that the liquid may also be in contact with the first face 102 of the aerosolization element 100 while in the reservoir.

The aerosolization element may be constructed of a variety of materials, comprising metals, which may be electroformed to create apertures as the element is formed, as described, for example, in U.S. Pat. No. 6,235,177 assigned to the present assignee and incorporated by reference herein in its entirety. Palladium is believed to be of particular usefulness in producing an electroformed, multi-apertured aerosolization element, as well as in operation thereof to aerosolize liquids. Other metals that can be used are palladium alloys, such as PdNi, with, for example, 80 percent palladium and 20% nickel. Other metals and materials may be used without departing from the present invention. The aerosolization element may be configured to have a curvature, as in a dome shape, which may be spherical, parabolic or any other curvature. The aerosolization element may have a curvature over its majority, and this may be concentric with the center of the aerosolization element, thus leaving a portion of the aerosolization element as a substantially planar peripheral ring. The aerosolization element may be mounted on an aerosol actuator 112 having an aperture therethrough, and this may be done in such a manner that the curved or domed portion of the aerosolization element extends through the aperture of the aerosol actuator and the substantially planar peripheral ring of the aerosolization element abuts a face of the aerosol actuator. The face of the aerosol actuator 112 closest to the first face of the aerosolization element may similarly be referred to, by convention, as the first face 114 of the aerosol actuator. The face of the aerosol actuator 112 closest to the second face of the aerosolization element may likewise by convention be referred to as the second face 115 of the aerosol actuator. The aerosolization element may be affixed to the aerosol actuator 112 with by its substantially peripheral ring portion being mounted to the first face 114 of the aerosol actuator 112, with the dome of the aerosolization element extending through the aperture of the aerosol actuator toward the second face of the aerosol actuator and may extend beyond the second face of the aerosol actuator 112.

The aerosolization element may be vibrated in such a manner as to draw liquid through the apertures 106 of the aerosolization element 100 from the first face to the second face, where the liquid is expelled from the apertures as a nebulized mist. The aerosolization element may be vibrated by a vibratory element 130, which may be a piezoelectric element. The vibratory element may be mounted to the aerosol actuator, such that vibration of the vibratory element may be mechanically transferred through the aerosol actuator to the aerosolization element. The vibratory element may be annular, and may surround the aperture of the aerosol actuator, for example, in a coaxial arrangement. A circuitry may provide power from a power source, such as an internal battery, which may be rechargeable. A switch may be operable to vibrate the vibratory element and thus the aerosolization element, and aerosolization performed in this manner may be achieved within milliseconds of operation of the switch. Further, this manner of aerosolization provides full aerosolization with a substantially uniform particle size of mist being produced effectively instantaneously with operation of the switch. The switch may be operable by a pressure transducer, which may be positioned in the mouthpiece of the nebulizer. The pressure transducer may be in electrical communication with the circuitry, and a microprocessor may also be in electrical communication with the circuitry, and the microprocessor may interpret electrical signals from the pressure transducer, and may also operate the switch to begin aerosolization. In this manner, nebulization can begin substantially instantaneously with the inhalation of a user upon the mouthpiece. An example of such a sensor switch can be found in co-assigned and co-pending U.S. application Ser. No. 09/705,063 assigned to the present assignee, the entire content of which is hereby incorporated herein by reference.

Another transducer may be used to sense the absence or presence of liquid in the reservoir, by sensing, for example, a difference between vibration characteristics of the aerosolization element, such as, for example, differences in frequency or amplitude, between wet vibration and substantially dry vibration. In this manner, the circuitry, may, for example by way of the microprocessor, turn the vibration off when there is essentially no more liquid to aerosolize, i.e., when the end of the dose has been achieved, thus minimizing operation of the aerosolization element in a dry state. Likewise, the switch may prevent vibration prior to delivery of a subsequent dose into the reservoir. An example of such a switch is shown in co-assigned and co-pending U.S. application Ser. No. 09/805,498, the entire content of which is hereby incorporated herein by reference.

The microprocessor may also have a timing capability, such that once aerosolization begins, it proceeds for a predetermined time, after which aerosolization stops. In this manner, a particular regimen of breathing and aerosolization may be carried out. For example, a user may be instructed to inhale for five seconds while the timing is set to aerosolize for only the first four seconds of such a breath maneuver. This timing may be predetermined based on a particular drug and a particular target of the drug, such as, for example, the deep lung, which may be the target of administration for a systemic drug, such as insulin.

The circuitry may also operate visual signals to a user, such as the illumination of a light, a blinking of a light, or the illumination or blinking of one or more of a plurality of lights. Further, a plurality of lights in a plurality of colors may be used. For example, a light may be illuminated to inform the user that the main power to the device is on, such that once a breath is taken, the breath switch will operate the aerosolization element. Another light signal may inform the user that the selected dose has been received in the reservoir, thus informing the user that the nebulizer is ready for the user to take a breath through the mouthpiece. A light signal may also inform the user that aerosol delivery has stopped based on a predetermined time for aerosolization, and, likewise, a light signal may inform the user when a predetermined regimen time for inhalation has elapsed, whereupon the user may stop inhalation of a breath. Similarly, a light signal may inform the user that the end of dose has been reached, as, for example, described above, and that the aerosolization is no longer taking place. Such a signal light may conveniently be a different color than other signal lights. Accordingly, a user may be informed from this information that the user has completed inhaling the chosen dose, and additional inhalation is not needed.

The screw mechanism 50 may comprise an internally threaded nut, which can be moved rotationally but not longitudinally. The threaded nut may mate with an externally threaded rod, which may be the rod portion 61 of the plunger 60, which can be moved longitudinally but not rotationally. Thus, rotation of the nut may move the rod longitudinally. Rotation of the actuator may be linked to cause rotation of the nut, thus advancing the rod and plunger. The rotation of the actuator may be calibrated to correspond to a predetermined longitudinal distance that corresponds to a volume of liquid displaced by movement of the plunger against the vial by that longitudinal distance. The plunger, however, may be maintained at a fixed distance from the stopper 63, so that advancing the plunger by rotation of the actuator does not immediately result in the displacement of liquid from the vial. After the user determines that the correct dosage has been chosen, for example by observing the visual display showing the dose that will be displaced into the reservoir for aerosolization if actuation is carried out, the actuator is moved longitudinally the fixed distance X. Movement of actuator causes longitudinal movement of the nut, which in turn carries the rod longitudinal a distance of X. The plunger is moved the distance Y which corresponds to X+D. Because D will vary from dose to dose, the distance Y of the longitudinal travel of the plunger will also vary.

One example of such a scheme is illustrated in FIG. 6. As shown, the dosing mechanism 30 extends into the housing and has a central opening into which the plunger 60 is housed. The dosing mechanism 30 is rotatable about the actuator 40, and when the actuator 40 is depressed, the dosing mechanism 30 moves axially into the device housing. Coupled to the dosing mechanism 30 is a threaded nut 31 that is threadably connected to plunger 60 (that also has mating threads about its shaft). The plunger 60 also includes an elongate detent (not shown) that is axially slidable within a groove formed in a stop 32 that is fixed to the device housing. In this way, the plunger 60 may move axially through stop 32, but not rotationally. Further, a spring 33 is positioned between the nut 31 and the stop 32 to bias actuator in the home position.

In operation, the user rotates the dosing mechanism 30 to set the desired dose. In so doing, the nut 31 also rotates. However, since plunger the 60 is prevented from rotating due to the stop 32, it moves axially downward toward the vial, thus reducing the distance between plunger 60 and the vial. When the desired dose is set, the user pushes down on the actuator 40. In turn, the dosing mechanism 30 and the nut 31 are also axially moved downward. In so doing, the plunger 60 is moved down the same distance. The plunger 60 will therefore engage the vial and dispense the appropriate dose. The travel of the plunger 60 is stopped when the nut 31 hits the stop 32. The actuator 40 may then be released to return to the initial position.

Such screw mechanisms are known to those skilled in the art, and are described, for example, in U.S. Pat. Nos. 4,883, 472; 5,370,629; and 5,954,699 previously incorporated herein by reference.

Over the course of a user dispensing the contents of a vial, which may contain, for example, a one week supply of a drug, such as insulin, the plunger may have incrementally moved from its initial position near the actuator to a final position abutting the plunger which has been moved essentially to the forward-most portion of the vial (see FIGS. 7A and 7B). The plunger must return to its initial position to act upon a new vial. The screw mechanism 50 may have a release that permits the plunger to travel back to its original position. The release may have a lock to prevent inadvertent return of the plunger prior to exhaustion of a vial. An example of such a release and lock is described, for example, in U.S. Pat. No. 5,954,699 previously incorporated herein.

U.S. Pat. No. 5,954,699 discloses an unlocking slide attached to a rear section that is connected to an internal spreader bushing in the rear section, with shifting of the unlocking slide in distal direction causing the spreader bushing to be shifted in distal direction.

The spreader bushing surrounds a driving member and comprises four vertical tracks, which extend towards the proximal end of the spreader bushing outwardly at an angle. The tracks serve to accommodate cams of the threaded flanges. When the spreader bushing is in the proximal position, the threaded flanges surround a threaded rod. When the spreader bushing is moved to its distal position with the unlocking slide, the threaded flanges open as soon as their cams move over the angled section of the tracks and the threaded rod can be freely shifted in axial direction. A notched surface of the unlocking slide arranged on the main body fits into a counter notched surface on the proximal part of the spreader bushing.

In principle, the spreader bushing is retained in its proximal position by a spring. In order to release the threaded flange the user must actively shift the unlocking slide into its distal position by simultaneously pushing it down. During this process, the notched surface of the unlocking slide engages in the counter notched surface of the spreader bushing, moving it backwards. Because of this movement, the cams must run over corresponding outwardly extending tracks of the spreader bushing. This forced movement causes the threaded flanges to open and releases the threaded rod. When at the same time the injection device is held with a dosing button down, gravity causes the threaded rod to automatically fall back into its distal position. Upon releasing the unlocking slide, the spreader bushing slides forward again. At the same time the cams slide back in the tracks to their stop position in which the threaded flange is closed. The unlocking slide is moved into the proximal position.

Various alternative configurations to control the linear distance of travel of the plunger by rotation of a dosing mechanism may be employed without departing from the scope of the present invention. For example, rotation of the dosing mechanism may not cause longitudinal movement of the plunger, but instead such rotation of the dosing mechanism may cause a threaded member to move longitudinally to control the longitudinal distance the plunger may travel on actuation. Alternatively, rotation of the dosing mechanism may cause threaded members to cooperate with each other to lengthen or shorten the distance of longitudinal travel of the plunger or the screw mechanism, which may carry the plunger in longitudinal travel with a stroke of the actuator.

It should be appreciated that, the present invention may be practiced with alternative embodiments and with a variety of devices and methods. Accordingly, it should be appreciated that the foregoing is descriptive of the present invention and that certain changes or modifications may be made without departing from the scope of the present invention.

What is claimed is:

1. A method of delivering a nebulized fluid for inhalation, comprising:
    providing an aerosol generator;
    providing a container having a tab and containing a fluid to be nebulized;
    providing a reservoir assembly having a detent, comprising:
        a reservoir in fluid communication with the aerosol generator; and
        a cannula in fluid communication with the reservoir and the container;
    wherein the reservoir assembly engages the container by interlocking the detent and the tab to hold together the container and the reservoir assembly, providing a moveable member positioned to act upon the container in a manner to eject fluid therefrom;
providing a linkage mechanism operable through a range of operating positions that is coupled to the moveable member to selectively control a distance of movement of the moveable member;
selecting the distance of movement of the moveable member;
moving the moveable member to eject fluid from the container into the reservoir; and
operating the aerosol generator to eject fluid from the reservoir as a nebulized fluid for inhalation.

2. The method of claim 1, wherein the container defines a longitudinal axis and the moveable member is moveable in a direction substantially parallel to the longitudinal axis.

3. The method of claim 1, wherein the linkage mechanism comprises:
a dosing mechanism,
a screw mechanism, and
an actuator,
wherein the moveable member comprises a plunger,
wherein the dosing mechanism, the screw mechanism, the actuator, and the plunger together form a titration mechanism,
wherein the plunger is movable along a longitudinal axis within the titration mechanism,
wherein the actuator is movable a fixed distance X along the longitudinal axis defined by the plunger, and
wherein the dosing mechanism is rotatable in a plane substantially perpendicular to the longitudinal axis;
wherein the container comprises a vial mechanism, comprising:
a vial, the vial having a longitudinal axis; and
a movable seal movable along the longitudinal axis of the vial;
and further comprising:
inserting the vial mechanism into a housing coupled to the aerosol generator such that the longitudinal axis of the vial is substantially parallel to the longitudinal axis of the plunger;
rotating the dosing mechanism to select a dose;
operating the screw mechanism, by rotating the dosing mechanism, to set a variable distance of travel Y of the plunger corresponding to the selected dose the proviso that longitudinal travel of the plunger is not imparted;
moving the actuator longitudinally the fixed distance X to move the plunger longitudinally the selected variable distance Y to move a movable stopper the variable distance Y; and
displacing a volume of liquid, corresponding to the selected dose, from the vial to contact the aerosol generator.

4. The method of claim 3, wherein the aerosol generator comprises:
an aerosolization element having a first face and a second face, each face having a plurality of apertures therethrough,
wherein operating the aerosol generator comprises vibrating the aerosolization element.

5. The method of claim 3, further comprising coupling the reservoir to the aerosol generator, wherein the volume of liquid is displaced from the vial into the reservoir to contact the aerosol generator.

6. The method of claim 1,
wherein the moveable member comprises a longitudinally moveable plunger, movement thereof defining a longitudinal axis,
wherein the linkage mechanism comprises:
a longitudinally moveable actuator to move the plunger, movement of the actuator being along the longitudinal axis;
a screw mechanism to set a distance of travel of the plunger; and
a rotatably mounted dosing mechanism, rotation thereof defining an axis of rotation; and
wherein the container comprises a vial mechanism, comprising:
a vial along the longitudinal axis; and
a moveable seal being moveable along the longitudinal axis.

7. The method of claim 6, further comprising:
providing a controller to control operation of the aerosol generator;
placing the vial mechanism within a housing coupled to the aerosol generator such that the longitudinal axis of the vial is substantially coaxial with the axis of rotation of the dosing mechanism;
rotating the dosing mechanism to select a dose; and
moving the actuator to move the plunger such that fluid is dispensed from the vial.

* * * * *